US005087750A

United States Patent [19]

Uda et al.

[11] Patent Number: 5,087,750

[45] Date of Patent: Feb. 11, 1992

[54] PROCESS FOR PRODUCING ALPHA-HYDROXYISOBUTYRIC ACID AMIDE

[75] Inventors: Akitomo Uda; Shuji Ebata; Hirofumi Higuchi, all of Niigata, Japan

[73] Assignee: Mitsubishi Gas Chemical Company, Inc., Tokyo, Japan

[21] Appl. No.: 586,802

[22] Filed: Sep. 24, 1990

[30] Foreign Application Priority Data

Dec. 19, 1989 [JP] Japan ........ 1-327346

[51] Int. Cl.[5] ........ C07C 231/06

[52] U.S. Cl. ........ 564/126

[58] Field of Search ........ 564/126; 585/640

[56] References Cited

U.S. PATENT DOCUMENTS

| | | | |
|---|---|---|---|
| 1,895,529 | 1/1933 | Taylor et al. | 585/640 |
| 3,699,164 | 10/1972 | Fine et al. | 564/126 |
| 4,018,829 | 4/1977 | Gruber et al. | 260/561 B |
| 4,049,573 | 9/1977 | Kaeding | 585/640 |
| 4,950,801 | 8/1990 | Ebata et al. | 564/126 |
| 4,987,256 | 1/1991 | Ebata et al. | 564/126 |

FOREIGN PATENT DOCUMENTS

| | | | |
|---|---|---|---|
| 0051984 | 5/1982 | European Pat. Off. | 564/126 |
| 63-57534 | 3/1988 | Japan . | |
| 63-57535 | 3/1988 | Japan . | |
| 1351530 | 5/1974 | United Kingdom . | |

*Primary Examiner*—Glennon H. Hollrah
*Assistant Examiner*—P. O'Sullivan
*Attorney, Agent, or Firm*—Frishauf, Holtz, Goodman & Woodward

[57] ABSTRACT

A process for producing α-hydroisobutyric acid amide by a hydration reaction of acetonecyanohydrin in the presence of a catalyst containing manganese dioxide as a main component, and also in the presence of an oxidizing agent. In accordance with the process, the service life of the catalyst is increased, and the α-hydroxyisobutyric acid amide is produced in a high yield.

15 Claims, No Drawings

PROCESS FOR PRODUCING ALPHA-HYDROXYISOBUTYRIC ACID AMIDE

BACKGROUND OF THE INVENTION

1. Field of the Invention

The present invention relates to a process for producing α-hydroxyisobutyric acid amide by a hydration reaction of acetonecyanohydrin. α-Hydroxyisobutyric acid amide is a useful intermediate for production of methacrylamide and methyl methacrylate.

2. Description of Related Arts

A hydration reaction of acetonecyanohydrin in which α-hydroxyisobutyric acid amide is synthesized in the presence of a sulfuric acid catalyst, and then converted into methacrylamide and methyl methacrylate is well known, as described in, for example, Kirk Othmer "Encyclopedia of Chemical Technology", 3rd Ed., Vol. 15, p. 357. This process is widely carried out on a commercial scale.

The conventional process, however, has disadvantages in that large amounts of waste sulfuric acid and acidic ammonium sulfate are by-produced and the treatment thereof increases production costs of methyl methacrylate.

In order to solve the above disadvantages, various hydration reactions of acetonecyanohydrin using a solid catalyst in place of sulfuric acid have been proposed. As catalysts for the hydration reaction, Japanese Patent Application Laid-Open No. 4068/1972, for example, discloses that a manganese dioxide catalyst is effective, and Japanese Patent Application Laid-Open Nos. 222/1977, 57534/1988 and 57535/1988 disclose that a catalyst containing manganese dioxide as a main component (hereinafter referred to as a "manganese catalyst") is effective.

It is described that, in accordance with these methods, α-hydroxyisobutyric acid amide can be obtained in a yield of 60% to 95% by carrying out a hydration reaction of acetonecyanohydrin at 40° C. to 100° C. in the presence of a manganese catalyst, preferably in the presence of an acetone solvent, according to the following equation.

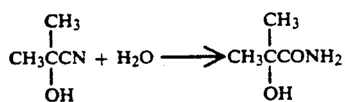

In fact, however, it has been found that in the hydration reaction using the above known manganese catalysts, the yield of α-hydroxyisobutyric acid amide is unsatisfactorily low for industrial use, the catalytic activity is lowered with a lapse of time, although it is high at the initial stage, leading to a rapid decrease in the yield of α-hydroxyisobutyric acid amide, and thus a stable operation on a commercial scale cannot be expected.

A tubular reactor was packed with a known manganese catalyst, and a feed solution prepared by adding water and a solvent to a distilled reagent acetonecyanohydrin was continuously introduced into the tubular reactor to conduct a reaction. By an analysis of the product solution from the outlet, changes with a lapse of time in the reaction results and the catalyst activity were measured. In the case of the known catalysts, the yield of α-hydroxyisobutyric acid amide at the initial stage of the reaction was relatively high, but this catalyst activity was rapidly decreased with a lapse of time, leading to unsatisfactory results for commercial use.

SUMMARY OF THE INVENTION

The object of the present invention is to provide a manganese catalyst having a sufficiently long lifetime.

It has been found that in a reaction of synthesizing α-hydroxyisobutyric acid amide from acetonecyanohydrin and water in the presence of a manganese catalyst, the lifetime of the catalyst and the reaction results can be markedly improved by carrying out the reaction in the presence of an oxidizing agent.

The present invention relates to a process for producing α-hydroxyisobutyric acid amide by hydrating acetone-cyanohydrin in the presence of a catalyst containing manganese as a main component, and also in the presence of an oxidizing agent.

DESCRIPTION OF PREFERRED EMBODIMENTS

The reaction of the present invention can be carried out batchwise or continuously. Industrially, a continuous reaction using a fixed bed catalyst or a slurry catalyst is employed, and particularly a continuous reaction using a fixed bed catalyst is preferred.

As the manganese catalysts, those disclosed in the known literatures can be used. In general, a manganese catalyst containing amorphous $\delta$-$MnO_2$ as a main component is suitable. The manganese catalyst as a fixed bed catalyst is used in a bulky form, or in a tablet form, or an extruded form.

The reaction temperature is 30° C. to 100° C. and preferably 40° C. to 80° C. At lower temperatures than 30° C., the rate of reaction is decreased. On the other hand, at higher temperatures than 100° C., the amounts of by-products resulting from decomposition of acetonecyanohydrin are undesirably increased.

The hydration reaction of the present invention is a liquid phase reaction. It is, therefore, preferred to control a reaction pressure so as to keep the reaction system in a liquid phase. Usually the reaction is carried out under atmospheric pressure, or under a pressure of not more than 2 $kg/cm^2G$.

In the present invention, the reaction is usually carried out in a system in which there is an excess of water. The proportion of acetonecyanohydrin in the feed solution is 10% to 60% by weight and preferably 20% to 50% by weight. If acetone is present in the feed solution in a concentration of 5% to 60% by weight, decomposition of acetonecyanohydrin as a side reaction is inhibited and, as a result, the yield of α-hydroxyisobutyric acid amide is desirably increased.

As oxidizing agents to be used in the present invention, oxygens such as oxygen and ozone, permanganic acid salts such as potassium permanganate, sodium permanganate, and lithium permanganate, chromic acid salts such as potassium chromate, sodium chromate, ammonium chromate, and potassium perchlorate, peroxides such as hydrogen peroxide, sodium peroxide, potassium peroxide, magnesium peroxide, calcium peroxide, barium peroxide, benzoyl peroxide, and diacetyl peroxide, peracids or peracid salts such as performic acid, peracetic acid, sodium persulfate, ammonium persulfate, and potassium persulfate, and oxyacids or oxyacid salts such as periodic acid, potassium periodate, sodium periodate, perchloric acid, potassium perchlorate, sodum perchlorate, potassium chlorate, sodium chlorate, potassium bromate, sodium iodate, iodic acid and sodium hypochlorate are preferred. Particularly oxygen, peroxides oxyacid, and oxyacid salts are suitable.

When oxygen is used as the oxidizing agent of the present invention, pure oxygen can be used. Usually oxygen is used after diluting with inert gas such as nitrogen. Of course, air can be used as it is, or a mixture of air and oxygen or inert gas can be used. .

The oxygen concentration of the oxygen-containing gas is not critical, and the oxygen concentration is preferably 2% to 50%. The amount of the oxygen-containing gas should be controlled in order that the ratio of the pure oxygen to the acetonecyanohydrin (ACH), i.e., the molar ratio of $O_2$ to ACH ($O_2$/ACH) is 0.001 to 0.1 and preferably 0.002 to 0.01.

When an oxygen gas is used as the oxidizing agent, it is particularly preferred to employ a so-called trickle bed type reaction in which the manganese catalyst is packed as a fixed bed and the reaction solution drops between the solid phase and the gas phase. This type of reactor permits good dispersion of gas in liquid and good contact with the catalyst. The flow of the solution and the flow of the oxygen-containing gas in the reactor can be cocurrent or counter-current.

When an peroxide, an oxyacid, or an oxyacid salt is used as the oxidizing agent, it is usually supplied after being dissolved in the feed solution.

These oxidizing agents can be used singly or in combination with each other.

The amount of the oxidizing agent added is such that as an effective oxygen, $O_2$/ ACH (molar ratio) is 0.001 to 0.1 and preferably 0.002 to 0.01.

In accordance with the process of the present invention, the reaction of synthesis of α-hydroxyisobutyric acid amide from acetonecyanohydrin and water in the presence of a catalyst containing manganese oxide as a main component is carried out in the coexistence of an oxidizing agent. This oxidizing agent greatly increases the service lifetime of the catalyst, and increases the yield. Thus, the process of the present invention is of high industrial significance.

The present invention is described in greater detail with reference to the following examples.

EXAMPLE 1

A jacketed Pyrex tubular reactor (inner diameter 10 mm, length 20 cm) was packed with 4 grams of a 20–32 mesh manganese dioxide catalyst (δ-$MnO_2$, prepared by the description of P. W. Selwood et al., J. Am. Chem. Soc., 71 3039 (1949)), and hot water maintained at 60° C. was passed through the jacket. A feed solution prepared by mixing 20 grams of acetonecyanohydrin, 60 grams of water, and 20 grams of acetone was introduced into the reactor at a rate of 5 grams per hour (g/hr), and air was introduced into the reactor from the upper portion thereof at a rate of 40 milliliters per hour (ml/hr). The reaction solution falling down from the catalyst layer was, after separation of air, collected at predetermined time intervals, and analyzed. Based on the yield of α-hydroxyisobutyric acid amide, a change with a lapse of time of catalytic activity was determined. The yields of α-hydroxyisobutyric acid amide after a 5 hour reaction and a one week reaction were 97% and 95%, respectively.

COMPARATIVE EXAMPLE 1

The reaction was carried out under the same conditions as in Example 1 except that no air was introduced.

The yields of α-hydroxyisobutyric acid amide after a 5 hour reaction and a one week reaction were 96% and 32%, respectively.

COMPARATIVE EXAMPLE 2

The reaction was carried out under the same conditions as in Example 1 except that nitrogen was passed at a rate of 40 ml/hr in place of air.

The yields of α-hydroxyisobutyric acid amide after a 5 hour reaction and a one week reaction were 96% and 14%, respectively.

EXAMPLE 2

The reaction was carried out under the same conditions as in Example 1 except that $H_2O_2$ was added to the feed solution in a concentration of 0.1% by weight and supplied in place of air.

The yields of α-hydroxyisobutyric acid amide after a 5 hour reaction and a one week reaction were 95% and 96%, respectively.

EXAMPLE 3

The reaction was carried out under the same conditions as in Example 1 except that sodium hypochlorate was added to the feed solution in a concentration of 0.2% by weight and supplied in place of air.

The yields of α-hydroxyisobutyric acid amide after a 5 hour reaction and one week reaction were 95% and 78%, respectively.

What is claimed is:

1. In a process for producing αo-hydroxyisobutyric acid amide by a hydration reaction of acetonecyanohydrin in the presence of a catalyst comprising manganese dioxide as a main component, the improvement which comprises carrying out the reaction in the presence of at least one oxidizing agent selected from the group consisting of oxygens, oxides, oxyacids and oxyacid salts, said oxidizing agent in an amount such that a molar ratio of effective oxygen to the acetonecyanohydrin is 0.001 to 0.1.

2. The process as defined in claim 1 wherein the reaction is carried out at a temperature of 30° C. to 100° C.

3. The process as defined in claim 1 wherein the reaction is carried out under such a pressure as to keep the reaction system in a liquid phase.

4. The process as defined in claim 1 wherein the reaction is carried out under atmospheric pressure or under a pressure of not more than 2 $kg/cm^2$.

5. The process as defined in claim 1 wherein the reaction is carried out in the presence of an excess of water.

6. The process as defined in claim 1 wherein a concentration of acetonecyanohydrin in the feed solution is 10% to 60% by weight.

7. The process as defined in claim 1 wherein acetone is present in a feed solution and the acetone has a concentration in the feed solution of 5% to 60% by weight.

8. The process as defined in claim 2, wherein the reaction is carried out at a pressure to maintain the reaction system in a liquid phase, said pressure being atmospheric pressure or a pressure not more than 2 $kg/cm^2$; the reaction is carried out in the presence of an excess of water; the concentration of acetonecyanohydrin in the feed solution is 10% to 60% by weight; and acetone is present in the feed solution and the acetone has a concentration in the feed solution of 5% to 60% by weight.

9. The process as defined in claim 1 wherein the oxidizing agent is selected from the group consisting of pure oxygen, ozone, oxygen diluted with inert gas, potassium permanganate, sodium permanganate, lithium permanganate, potassium chromate, sodium chromate, ammonium chromate, potassium perchlorate, hydrogen peroxide, calcium peroxide, potassium peroxide, magnesium peroxide, calcium peroxide, barium peroxide, benzoyl peroxide, diacetyl peroxide, periodic acid, potassium periodate, sodium periodate, perchloric acid, potassium perchlorate, sodium perchlorate, potassium chlorate, sodium chlorate, potassium bromate, sodium iodate, iodic acid and sodium hypochlorate.

10. The process as defined in claim 1 wherein the oxidizing agent is air.

11. The process as defined in claim 9, wherein the reaction is carried out at a temperature of 40° C. to 80° C.

12. The process as defined in claim 11, wherein the acetonecyanohydrin is in a feed solution in an amount of 20% to 50% by weight.

13. The process as defined in claim 12, wherein the amount of said oxidizing agent is such that a molar ratio of effective oxygen to the acetonecyanohydrin is 0.0002 to 0.01.

14. The process as defined in claim 13, wherein the process is conducted in the presence of an excess of water and in the presence of acetone and said acetone is in the feed solution in a concentration of 5% to 60% by weight.

15. The process as defined in claim 14, wherein the oxidizing agent is an oxygen diluted with inert gas comprising 2% to 50% oxygen.

* * * * *